(12) United States Patent
Stoltefuss et al.

(10) Patent No.: US 6,867,206 B1
(45) Date of Patent: Mar. 15, 2005

(54) 6-CARBOXYPHENYLDIHYDROPY-RIDAZINONE DERIVATIVES AND USE THEREOF

(75) Inventors: Jürgen Stoltefuss, Haan (DE);
Gabriele Bräunlich, Wuppertal (DE);
Michael Lögers, Wuppertal (DE);
Carsten Schmeck, Wuppertal (DE);
Ulrich Nielsch, Düsseldorf (DE);
Martin Bechem, Wuppertal (DE);
Christoph Gerdes, Leverkusen (DE);
Michael Sperzel, Wuppertal (DE);
Klemens Lustig, Wuppertal (DE);
Werner Stürmer, Remscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,927

(22) PCT Filed: Jun. 16, 2000

(86) PCT No.: PCT/EP00/05564

§ 371 (c)(1),
(2), (4) Date: Apr. 10, 2002

(87) PCT Pub. No.: WO01/00589

PCT Pub. Date: Jan. 4, 2001

(30) Foreign Application Priority Data

Jun. 29, 1999 (DE) .......................... 199 29 782

(51) Int. Cl.[7] .............. A61K 31/50; A61K 31/501; A61K 31/5377; C07D 237/04; C07D 401/10

(52) U.S. Cl. .............. 514/236.5; 514/247; 514/252.03; 514/252.05; 514/252.06; 544/114; 544/238; 544/239

(58) Field of Search .................. 544/238, 239, 544/114; 514/247, 236.5, 252.03, 252.05, 252.06

(56) References Cited

U.S. PATENT DOCUMENTS 3,689,652 A    9/1972    Curran et al. ............... 424/250

FOREIGN PATENT DOCUMENTS

DE    2150436    4/1972
EP    0258435    8/1987

OTHER PUBLICATIONS

Curran et al. J.Med. Chem. vol. 17, p. 273–281 (1974).*
Advanced Organic Chemistry by Jerry March (2nd Ed.) pp. 382–383 and 398–399 (1977).*
McEvoy et al., J. Med. Chem. vol. 17, p. 281–286 (1974).*
Chemical Abstracts, vol. 109, No. 25, 1988, Columbus, Ohio, US; abstract No. 231045d, p. 866; XP002153208.
Pschyrembel, Klinisches Worterbuch, Walter de Gruyter, Berlin.New York 2002, 1994, pp. 64–67.
Puhler, Regitz & Schmid, Rompp Lexikon Chemie, ver. 1.5, Georg Thieme Verlad, Stuttgart. New York, 1998, p. 33.
Kuschinsky, Lullmann & Peters, Kurzes Lehrbuch der Pharmakologie und Toxikologie, 9, Auflage, Georg Thieme Verlag Stuttgart, 1981, pp. 139–142.
Mutschler, Arzneimittel–wirkungen, Lehrbuch der Pharmakologie und Toxikologie, Wissenschaftliche Verlagsgesellschaft mbH Stuttgart, 1996, pp. 406–409.
Eckardt, K., "Erythropoietin: Karriere eines Hormons", Deutsches Arzteblatt, 95: A–285–A290 (1998).
Rote Liste 2000, Editio Cantor Verlag, Aulendorf, 2000, "Epoetin alfa" und "Epoetin beta".

* cited by examiner

Primary Examiner—Emily Bernhardt

(57) ABSTRACT

The present invention relates to 6-carboxyphenyldihydropyridazinone derivatives having the formula (I)

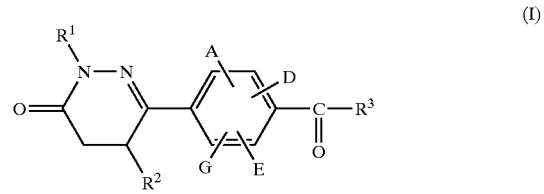

wherein $R^1$, $R^2$, $R^3$, A, D, G, and E are as defined in the specification and claims, a process for preparing these materials, pharmaceutical compositions containing them, and a method for using them in the treatment of anemias.

14 Claims, No Drawings

6-CARBOXYPHENYLDIHYDROPY-RIDAZINONE DERIVATIVES AND USE THEREOF

This application is the national stage filing under 35 U.S.C. §371 of International Application PCT/EP00/05564, filed 16 Jun. 2000, which claims the priority of German application serial number 199 29 782.7, filed 29 Jun. 1999.

The present invention relates to the field-of-erythropoiesis. In particular, the present invention relates to novel 6-carboxyphenyldihydropyridazinone derivatives, to processes for preparing them and to their use as medicaments, preferably for the prophylaxis and/or control of anemias.

Anemias are characterized by the erythrocyte count, hemoglobin concentration and/or hematocrit decreasing below the age-related and sex-specific reference values. However, a decrease in one of these parameters is only a sign of an anemia when the blood volume is normal but not when the decrease is associated with acute, relatively marked blood losses, exsiccosis (pseudopolyglobulism) or hydremia (pseudoanemnia). (Pschyrembel, Klinisches Wörterbuch Clinical Dictionary, 257th edition, 1994, Walter de Gruyter Verlag, page 59 ff., entry "Anemia"; Römpp Lexikon Chemie [Römpp Chemistry Encyclopedia], version 1.5, 1998, Georg Thieme Verlag Stuttgart, entry "Anemia").

As a consequence of the decreased capacity of the blood to transport oxygen, anemia is characterized clinically by, inter alia, disturbances in oxygen-dependent metabolism and organ functions; when the anemia develops acutely, for example as a consequence of the loss of blood, shock symptoms can appear, and, when it develops chronically, there is frequently a slowly progressing course associated with decline in performance, tiredness, dyspnea and tachycardia.

The different forms of anemia can be subdivided or classified either in accordance with the morphology and hemoglobin content of the erythrocytes or in accordance with etiology (for example into posthemorrhagic anemia, pregnancy anemia, tumor anemia, infection anemia and deficiency anemias). It is furthermore possible to subdivide the different forms of anemia in accordance with their pathogenesis while taking into consideration the causes which are in principle possible, for example into anemias caused by excessive loss of blood (for example acute or chronic hemorrhagic anemia), anemias resulting from reduced or ineffective erythropoiesis (for example iron deficiency anemias, nephrogenic anemias or myelopathic anemias) and anemias resulting from excessive erythrocyte breakdown (what are termed hemolytic anemias) (Pschyrembel, Klinisches Wörterbuch, 257th edition, 1994, Walter de Gruyter Verlag, page 59 ff., entry "anemia"; Roche-Lexikon Medizin [Roche Medical Encyclopedia], 4th edition, 1999, Urban & Schwarzenberg, entry "anemia").

In practice, the methods for treating anemias which are disclosed in the prior art prove to be very difficult and not particularly efficient. Large numbers of side-effects, which are frequently serious to the patient, usually occur.

Thus, in the therapy of iron deficiency anemias, use is generally made of iron preparations which are administered either orally or parenterally. When they are administered orally, it is, in particular, gastrointestinal disturbances which are observed as side-effects. The simultaneous administration of antacids, for the purpose of treating the gastrointestinal disturbances, impairs absorption of the iron. Furthermore, the absorption of iron from the intestinal tract is in any case only very limited because of the ability of the mucosa to impede the passage of iron. On the other hand, a dose which is administered orally should not be too high because, if it is, symptoms of poisoning can then occur, in the worst case even a hemorrhagic gastroenteritis which is associated with shock symptoms and leads to death. Administration of the iron therapy parenterally, which likewise proves to be difficult because of the plasma only having a low ability to bind iron, can lead, particularly when an overdose is given, to nausea, vomiting, cardialgias and headaches, heat sensations and a severe fall in blood pressure associated with collapse, and, furthermore, to the deposition of iron in the reticuloendothelium (hemosiderosis); the blood vessel walls are damaged by the intravenous injection and thrombophlebitis and clot formation must be expected. Dosing proves to be extremely difficult since all the iron which cannot be bound physiologically when it is administered parenterally then has a toxic effect (Gustav Kuschinsky, Heinz Lüllmann and Thies Peters, Kurzes Lehrbuch der Pharmakologie und Toxikologie [Short Textbook of Pharmacology and Toxicology], 9th edition, 1981, Georg Thieme Verlag Stuttgart, pages 139 ff.; Ernst Mutschler, Arzneimittelwirkungen, Lehrbuch der Pharmakologie und Toxikologie [Effects of Pharmaceuticals, Textbook of Pharmacology and Toxicology], Wissenschaftliche Verlagsgesellschaft mbH Stuttgart, 1986, pages 383 ff.).

For somewhat more than 10 years now, recombinant erythropoietin (rhEPO), which is prepared by genetic manipulation, has been available for therapeutic employment for treating severe anemias. This is because, it is known that recombinant human (rh) EPO stimulates erythropoiesis humorally, as a result of which it has come to be used as an antianemic agent in the therapy of severe anemias, particularly in renal and nephrogenic anemias. In addition, rh EPO is used for increasing the number of endogenous blood cells in order to decrease the requirement for transfusions of foreign blood.

Erythropoietin (EPO) is a glycoprotein which has a molecular weight of about 34 000 Da. More than 90% of the EPO is synthesized in the kidney, and the EPO which is produced in this organ is secreted into the blood. The primary physiological function of EPO is that of regulating erythropoiesis in the bone marrow. In this location, EPO stimulates the proliferation and maturation of the erythrocytic precursor cells.

However, powerful side-effects occur when rh EPO is administered. These side effects include the development and amplification of high blood pressure and the causation of an encephalopathy-like symptomatology, leading all the way to tonic/clonic convulsions and cerebral or myocardial infarction due to thromboses. Furthermore, rh EPO is not available orally and has therefore to be administered intraperitoneally (i.p.), intravenously (i.v.) or subcutaneously (s.c.), thereby restricting its use to the therapy of severe anemias (Kai-Uwe Eckardt, "Erythropoietin: Karriere eines Hormons" [Career of a Hormone], Deutsches Ärzteblatt 95, issue 6 dated Feb. 6, 1998 (41), pages A-285 to A-290; Rote Liste [Red List] 1998, Editio Cantor Verlag für Medizin und Naturwissenschaften GmbH, see "Epoetin alpha" and "Epoetin beta").

The object of the present invention is now to provide novel substances which are particularly suitable for treating anemias more efficiently and which, in this connection, avoid the disadvantages of the methods for treating anemias which are known from the prior art.

The present invention consequently relates to 6-carboxyphenyldihydropyridazinone derivatives of the general formula (I)

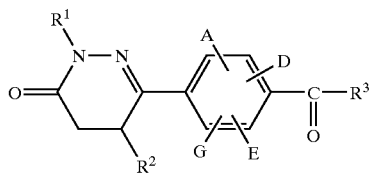
(I)

in which
A, D, E and G are identical or different and represent hydrogen, halogen, trifluoromethyl or hydroxyl, or represent $(C_1-C_6)$-alkyl or represent $(C_1-C_6)$-alkoxy,
$R^1$ and $R^2$ are identical or different and represent hydrogen or represent $(C_1-C_6)$-alkyl,
$R^3$ represents radicals of the formulae —$OR^4$ or —$NR^5R^6$, in which
$R^4$ denotes cycloalkyl having from 3 to 8 carbon atoms or $(C_1-C_8)$-alkyl which is optionally substituted by hydroxyl, $(C_1-C_6)$-alkoxy, cycloalkyl having from 3 to 8 carbon atoms or aryl having from 6 to 10 carbon atoms which, for its part, can be substituted, once to twice, identically or differently, by substituents which are selected from the group: halogen, $(C_1-C_6)$-alkoxy, hydroxyl or trifluoromethyl, or denotes $(C_1-C_6)$-alkyl which is optionally substituted by a group of the formula —$NR^7R^8$,
in which
$R^7$ and $R^8$ are identical or different and denote hydrogen, $(C_1-C_6)$-alkyl or benzyl, or
$R^4$ denotes vinyl or allyl, or
$R^4$ denotes aryl having from 6 to 10 carbon atoms which is optionally substituted, once to twice, identically or differently, by substituents which are selected from the group consisting of: halogen, $(C_1-C_6)$-alkyl, $(C_1-C_6)$-alkoxy or hydroxyl,
$R^5$ denotes hydrogen or $(C_1-C_4)$-alkyl,
$R^6$ denotes cycloalkyl having from 3 to 8 carbon atoms or a radical of the formula

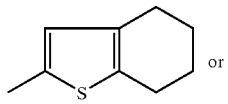 or aryl having from 6 to 10 carbon atoms or a 5- to 7-membered aromatic heterocycle having up to 3 heteroatoms from the series S, N and/or O, it being possible for the ring systems which are listed here to be optionally substituted, once to several times, identically or differently, by substituents which are selected from the group: halogen, trifluoromethyl, hydroxyl, $(C_1-C_6)$-alkoxy, carboxyl, $(C_1-C_6)$-alkoxycarbonyl, $(C_1-C_6)$-alkyl and radicals of the formulae —$SO_2$—$NR^9R^{10}$ and —$(CO)_a$—$NR^{11}R^{12}$,
in which
$R^9$, $R^{10}$, $R^{11}$ and $R^{12}$ are identical or different and denote hydrogen or $(C_1-C_6)$-alkyl, and
a denotes a number 0 or 1, or
$R^6$ denotes $(C_1-C_6)$-alkyl which is optionally substituted, once to twice, identically or differently, by substituents which are selected from the group: halogen, trifluoromethyl, hydroxyl, $(C_1-C_6)$-alkoxy, carboxyl, $(C_1-C_6)$-alkoxycarbonyl and aryl having from 6 to 10 carbon atoms and from 5- to 7-membered aromatic heterocycles having up to 3 heteroatoms from the series S, N and/or O, in which the ring systems can be optionally substituted, once to three times, identically or differently, by $(C_1-C_6)$-alkyl, halogen, $(C_1-C_6)$-alkoxy, $(C_1-C_6)$-alkoxycarbonyl, trifluoromethyl or by the radical —CO—$NH_2$, or
$R^5$ and $R^6$ form, together with the nitrogen atom, cyclic radicals of the formulae

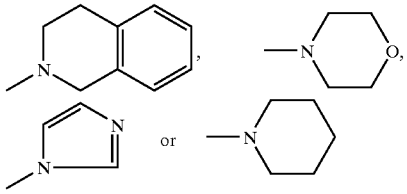

which, for their part, can be optionally substituted, and the salts thereof.

Depending on the substitution pattern, the compounds according to the invention can exist in stereoisomeric forms which either relate to each other as image and mirror image (enantiomers) or which do not relate to each other as image and mirror image (diastereomers). The invention relates both to the enantiomers or diastereomers and to their respective mixtures. The racemic forms, like the diastereomers, can be resolved, in a known manner, into the stereoisomerically uniform constituents.

Physiologically harmless salts of the compounds according to the invention can be salts of the substances according to the invention with mineral acids, carboxylic acids or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalene-disulfonic acid, acetic acid, propionic acid, lactic acid, tartaric acid, citric acid, fumaric acid, maleic acid or benzoic acid.

Salts which may be mentioned are also salts with customary bases, for example alkali metal salts (e.g. sodium or potassium salts), alkaline earth metal salts (e.g. calcium or magnesium salts) or ammonium salts derived from ammonia or organic amines such as diethylamine, triethylamine, ethyl diisopropylamine, procaine, dibenzylamine, N-methylmorpholine, dihydroabietylamine, 1-ephenamine or methyl-piperidine.

$(C_3-C_8)$-Cycloalkyl represents cyclopropyl, cyclopentyl, cyclobutyl, cyclohexyl, cycloheptyl or cyclooctyl. Cyclopropyl, cyclopentyl and cyclohexyl may be mentioned as being preferred.

$(C_6-C_{10})$-Aryl represents an aromatic radical having from 6 to 10 carbon atoms. Preferred aryl radicals are phenyl and naphthyl.

$(C_1-C_6)$-Alkyl represents a straight-chain or branched alkyl radical having from 1 to 6 carbon atoms. Examples which may be mentioned are: methyl, ethyl, n-propyl, isopropyl, n-butyl, isobutyl, tert-butyl, n-pentyl and n-hexyl. A straight-chain or branched alkyl radical having from 1 to 4 carbon atoms is preferred. A straight-chain or branched alkyl radical having from 1 to 3 carbon atoms is particularly preferred.

($C_1$–$C_6$)-Alkoxy represents a straight-chain or branched alkoxy radical having from 1 to 6 carbon atoms. Examples which may be mentioned are: methoxy, ethoxy, n-propoxy, isopropoxy, n-butoxy, isobutoxy, tert-butoxy, n-pentoxy and n-hexoxy. A straight-chain or branched alkoxy radical having from 1 to 4 carbon atoms is preferred. A straight-chain or branched alkoxy radical having from 1 to 3 carbon atoms is particularly preferred.

($C_1$–$C_6$)-Alkoxycarbonyl represents a straight-chain or branched alkoxycarbonyl radical having from 1 to 6 carbon atoms. Examples which may be mentioned are: methoxycarbonyl, ethoxycarbonyl, n-propoxycarbonyl, isopropoxycarbonyl, n-butoxycarbonyl, isobutoxycarbonyl and tert-butoxycarbonyl. A straight-chain or branched alkoxycarbonyl radical having from 1 to 4 carbon atoms is preferred. A straight-chain or branched alkoxycarbonyl radical having from 1 to 3 carbon atoms is particularly preferred.

A 5- to 6-membered aromatic heterocycle having up to 3 heteroatoms from the series S, O and/or N represents, for example, pyridyl, pyrimidyl, pyridazinyl, thienyl, furyl, pyrrolyl, thiazolyl, oxazolyl or imidazolyl. Pyridyl, thienyl, pyridazinyl, furyl and thiazolyl are preferred.

Preference is given to compounds of the general formula (I) according to the invention
in which
A, D, E and G are identical or different and represent hydrogen, fluorine, chlorine, bromine or trifluoromethyl,
$R^1$ and $R^2$ are identical or different and represent hydrogen or represent methyl,
$R^3$ represents radicals of the formulae —$OR^4$ or —$NR^5R^6$,
in which
$R^4$ denotes cyclopropyl, cyclopentyl or cyclohexyl or denotes ($C_1$–$C_6$)-alkyl which is optionally substituted by hydroxyl, ($C_1$–$C_4$)-alkoxy, cyclopropyl, cyclopentyl, cyclohexyl or phenyl which, for its part, can be substituted once to twice, identically or differently, by substituents selected from the group: fluorine, chlorine, bromine, ($C_1$–$C_4$)-alkoxy, hydroxyl or trifluoromethyl, or denotes ($C_1$–$C_6$)-alkyl which is optionally substituted by a group of the formula —$NR^7R^8$,
in which
$R^7$ and $R^9$ are identical or different and denote hydrogen or ($C_1$–$C_4$)-alkyl, or
$R^4$ denotes allyl,
$R^5$ denotes hydrogen or ($C_1$–$C_3$)-alkyl,
$R^6$ denotes cyclopropyl, cyclopentyl or cyclohexyl or denotes phenyl, thienyl, thiazolyl, furyl or pyridyl, it being possible for the listed aromatic ring systems to be optionally substituted, once to twice, identically or differently, by substituents selected from the group: fluorine, chlorine, bromine, trifluoromethyl, hydroxyl, ($C_1$–$C_3$)-alkoxy, ($C_1$–$C_3$)-alkoxycarbonyl, ($C_1$–$C_4$)-alkyl and radicals of the formulae —$SO_2NR^9R^{10}$ and —$(CO)_a$—$NR^{11}R^{12}$,
in which
$R^9$, $R^{10}$, $R^{11}$ and $R^{12}$ are identical or different and denote hydrogen or ($C_1$–$C_4$)-alkyl, and
a denotes a number 0 or 1, or
$R^6$ denotes ($C_1$–$C_6$)-alkyl which are optionally substituted once to twice, identically or differently, by substituents selected from the group: fluorine, chlorine, bromine, trifluoromethyl, hydroxyl, ($C_1$–$C_4$)-alkoxy, ($C_1$–$C_4$)-alkoxycarbonyl, phenyl, pyridyl, naphthyl, furyl or thiazolyl, it being possible for the ring systems to be optionally substituted, once to twice, identically or differently, by fluorine, chlorine, methyl, methoxycarbonyl, trifluoromethyl or by a radical of the formula —CO—$NH_2$, or $R^5$ and $R^6$ form, together with the nitrogen atom, cyclic radicals of the formulae

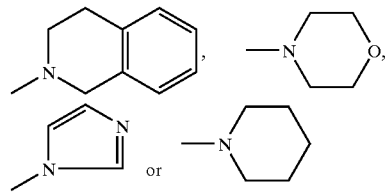

and the salts thereof.

Particular preference is given to compounds of the general formula (I) according to the invention
in which
A, D, E and G represent hydrogen,
$R^1$ and $R^2$ are identical or different and represent hydrogen or represent methyl,
$R^3$ represents radicals of the formulae —$OR^4$ or —$NR^5R^6$,
in which
$R^4$ denotes cyclopropyl, cyclopentyl or cyclohexyl or denotes ($C_1$–$C_5$)-alkyl which is optionally substituted by ($C_1$–$C_4$)-alkoxy, cyclopropyl, cyclopentyl, cyclohexyl or phenyl which, for its part, can be substituted, once to twice, identically or differently, by substituents selected from the group: fluorine, chlorine, ($C_1$–$C_4$)-alkoxy, hydroxyl or trifluoromethyl, or denotes ($C_1$–$C_4$)-alkyl which is optionally substituted by a group of the formula —$NR^7R^8$,
in which
$R^7$ and $R^8$ are identical or different and denote hydrogen, benzyl or methyl, or
$R^4$ denotes allyl,
$R^5$ denotes hydrogen or ($C_1$–$C_3$)-alkyl,
$R^6$ denotes cyclopropyl, cyclopentyl or cyclohexyl or denotes phenyl, naphthyl, thienyl, thiazolyl, furyl or pyridyl, with the listed ring systems being optionally substituted once to twice, identically or differently, by substituents selected from the group: fluorine, chlorine, bromine, trifluoromethyl, ($C_1$–$C_3$)-alkoxy, ($C_1$–$C_3$)-alkoxycarbonyl, ($C_1$–$C_3$)-alkyl and radicals of the formulae —$SO_2$—$NR^9R^{10}$ and —$(CO)_a$—$NR^{11}R^{12}$,
in which
$R^9$, $R^{10}$, $R^{11}$ and $R^{12}$ are identical or different and denote hydrogen or ($C_1$–$C_4$)-alkyl, and
a denotes a number 0 or 1, or
$R^6$ denotes ($C_1$–$C_6$)-alkyl which is optionally substituted by substituents selected from the group: fluorine, chlorine, trifluoromethyl, ($C_1$–$C_3$)-alkoxy, ($C_1$–$C_3$)-alkoxycarbonyl, phenyl, pyridyl, naphthyl, furyl, thienyl or thiazolyl, the ring systems optionally being substituted once to twice, identically or differently, by fluorine, chlorine, methyl, methoxycarbonyl or trifluoromethyl or by a radical of the formula —CO—$NH_2$, or
$R^5$ and $R^6$ form, together with the nitrogen atom, cyclic radicals of the formulae

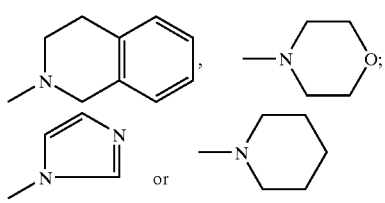, and the salts thereof.

Very particular preference is given to compounds of the general formula (I) according to the invention
in which
A, D, E and G represent hydrogen,
$R^3$ represents the radical —$NR^5R^6$, where $R^5$=H or methyl and $R^6$ is as previously defined,
and the remaining radicals have the previously mentioned meaning.

The present invention also relates to processes for preparing the compounds of the general formula (I) according to the invention, where
[A] in the case where $R^3$ represents the radical of the formula —$OR^4$ in the above general formula (I),
compounds of the general formula (II)

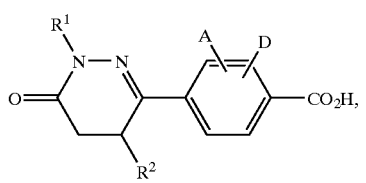

(II)

in which
A, D, $R^1$ and $R^2$ have the abovementioned meaning,
are initially converted, by reaction with carboxylic acid-activating reagents, such as thionyl chloride or carbonyldiimidazole and using customary methods, into the compounds of the general formula (IV)

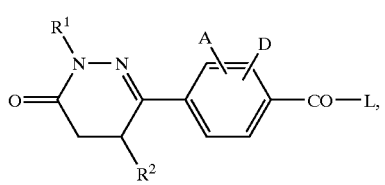

(IV)

in which
A, D, $R^1$ and $R^2$ have the abovementioned meaning, and
L represents an activating radical, preferably chlorine or imidazolyl,
and, in a second step, compounds are reacted with compounds of the general formula (III)

HO—$R^4$ (III).

in which
$R^4$ has the abovementioned meaning,
in inert solvents, where appropriate in the presence of a base, or
[B] in the case where $R^3$ represents the radical of the formula —$NR^5R^6$ in the above general formula (I),
compounds of the general formula (II) are initially converted, by reaction with carboxylic acid-activating reagents, such as thionyl chloride or carbonyldiimidazole, and using customary methods, into the compounds of the general formula (IV)

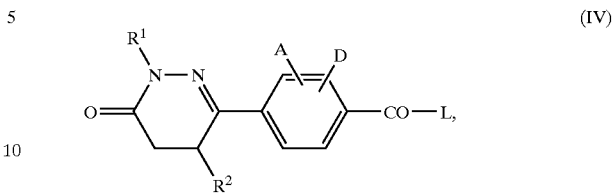

in which
A, D, $R^1$ and $R^2$ have the abovementioned meaning, and
L represents an activating radical, preferably chlorine or imidazolyl,
and, in a second step, reacted with amides of the general formula (V)

$HNR^5R^6$ (V), in which
$R^5$ and $R^6$ have the abovementioned meaning,
in inert solvents.

Within the meaning of the present invention, suitable carboxylic acid-activating reagents are, in particular, carbodiimides, such as diisopropylcarbodiimide, dicyclohexylcarbodiimide or N-(3-dimethylaminopropyl)-N'-ethylcarbodiimide hydro-chloride, or carbonyl compounds, such as carbonyldiimidazole, or 1,2-oxazolium compounds, such as 2-ethyl-5-phenyl-1,2-oxazolium-3-sulfonate, or propane-phosphoric acid anhydride or isobutyl chloroformate or benzotriazolyloxytris-(dimethylamino) phosphonium hexyfluorophosphate or diphenyl phosphonate amide or methanesulfonyl chloride, where appropriate in the presence of bases such as triethylamine or N-ethylmorpholine or N-methylpiperidine or dicyclohexylcarbodiimide and N-hydroxysuccinimide. Thionyl chloride is also suitable. Preferred carboxylic acid-activating reagents are carbonyldiimidazole (CDI) and thionyl chloride.

The methods according to the invention can be explained, by way of example, by means of the following formula schemes:

[A]

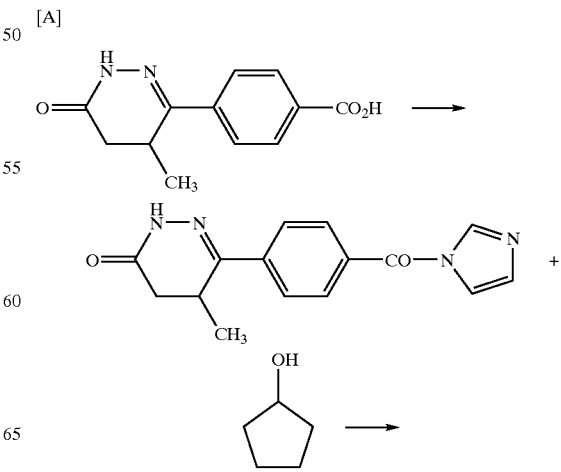

-continued

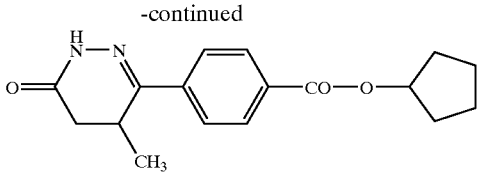
[B]

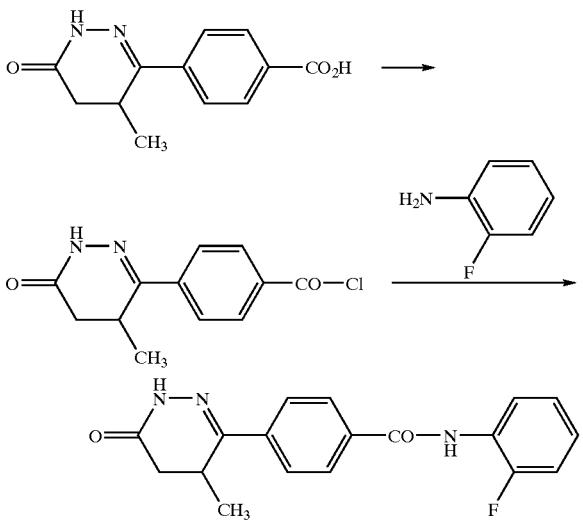

[B]

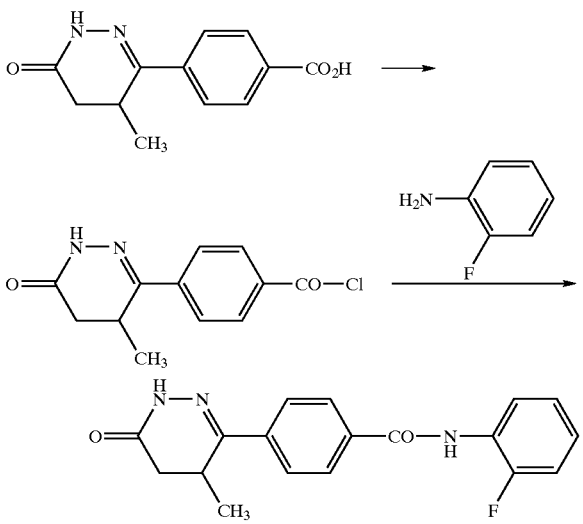

Suitable solvents in this connection are organic solvents which are inert under the reaction conditions. These include halogenohydrocarbons, such as dichloromethane, trichloromethane, tetrachloromethane, 1,2-dichloroethane, trichloroethane, tetrachloroethane, 1,2-dichloroethylene or trichloroethylene, hydrocarbons, such as benzene, xylene, toluene, hexane or cyclohexane, ethers, such as diethyl ether, dioxane or THF, and also dimethylformamide, acetonitrile, acetone or hexamethyl-phosphoric triamide. Dichloromethane, DMF and dioxane are particularly preferable. It is also possible to use solvent mixtures.

Suitable bases are the customary inorganic or organic bases. These preferably include alkali metal hydroxides, such as sodium or potassium hydroxide, or alkali metal carbonates, such as sodium or potassium carbonate, or sodium or potassium methoxide or sodium or potassium ethoxide or potassium tert-butoxide or amides, such as sodium amide, lithium bis(trimethylsilyl)amide or lithium diisopropylamide, or organometallic compounds, such as butyllithium or phenyllithium, and organic bases, such as triethylamide, pyridine, dimethylaminopyridine, 1,8-diazobicyclo-[5.4.0]undec-7-ene (DBU), 1,5-diazabicyclo [4.3.0]non-5-ene (DBU) or N-methyl-morpholine. Pyridine and triethylamine are preferred.

In this connection, the base can be employed in a quantity of from 1 to 5 mol, preferably of from 1 to 2 mol, based on 1 mol of the compounds of the general formula (II).

In general, the reaction takes place in a temperature range of from −78° C. up to reflux temperature, preferably in the range from −78° C. to +20° C.

The reaction can be carried out under normal, increased or decreased pressure (for example in the range from 0.5 to 5 bar). In general, the reaction is carried out under normal pressure.

The compounds of the general formulae (II), (III) and (V) are known per se or can be prepared using published methods [cf., with regard to compounds of the formula (II), J. Med. Chem. 17, (273–281), 1974].

Some of the compounds of the general formula (IV) are novel and can be prepared, for example, as described above.

The compounds of the general formula (I) according to the invention exhibit a valuable pharmacological spectrum of activity which was not foreseeable and are particularly suitable, therefore, for the prophylaxis and/or treatment of diseases.

They can preferably be employed in medicaments for the prophylaxis and/or treatment of anemias, such as in premature baby anemias, in nephrogenic or renal anemias, such as anemias associated with chronic renal insufficiency, in anemias following chemotherapy and in the anemia suffered by HIV patients, i.e. they can consequently be used, in particular, for treating severe anemias.

Even when the endogenous EPO production is completely intact, administration of the compounds according to the invention can induce an additional stimulation of erythropoiesis, something which can be exploited, in particular, in the case of individuals donating their own blood.

All the customary administration forms are suitable for administering the compounds according to the invention. The administration is preferably effected orally, transdermally or parenterally. Very particular preference is given to oral administration, which represents an additional advantage as compared with the therapy of anemias with rhEPO, as is known from the prior art.

The compounds according to the invention act, in particular, as erythropoietin sensitizers. "Erythropoietin sensitizers" is the term used for compounds which are able to influence the action of the EPO which is present in the body so efficiently that erythropoiesis is increased and, in particular, oxygen supply is improved. Surprisingly, the compounds are also active orally, thereby substantially improving and simultaneously simplifying therapeutic use while excluding or reducing the known side-effects.

The present invention thus also relates to the use of the EPO sensitizers for stimulating erythropoiesis, in particular for the prophylaxis and/or treatment of anemias, preferably severe anemias, such as premature baby anemia, anemia associated with chronic kidney insufficiency, anemia following chemotherapy or else anemia in HIV patients. Particular preference is given to administering the so-called EPO sensitizers orally for the abovementioned purposes.

Thus, the compounds according to the invention enable erythropoiesis to be stimulated efficiently and consequently make possible a prophylaxis and/or therapy of anemias which intervenes prior to the stage at which the conventional methods of treatment with EPO begin. This is because the compounds according to the invention enable the endogenous EPO to be influenced effectively, thereby making it possible to avoid direct administration of EPO together with the disadvantages associated therewith.

The present invention consequently also relates to medicaments and pharmaceutical compositions which comprise at least one compound of the general formula (I) according to the invention together with one or more pharmacologically harmless auxiliary or carrier substances, and also to their use for stimulating erythropoiesis, in particular for the purposes of prophylaxis and/or treatment of anemias, such as premature baby anemia, anemias associated with chronic renal insufficiency, anemias following chemotherapy or anemias in HIV patients.

The present invention will be illustrated by the following examples, which do not, however, limit the invention in any way.

A ASSESSMENT OF PHYSIOLOGICAL EFFICACY

1. General test methods
a) Test description (in vitro)
Proliferation of human erythrocytic precursor cells 20 ml of heparinized blood were diluted with 20 ml of PBS (phosphate-buffer saline) and centrifuged for 20 min (220×g). The supernatant was discarded and the cells were resuspended in 30 ml of PBS and pipetted onto 17 ml of Ficoll Paque® (d=1.077 g/ml, Pharmacia) in a 50 ml tube. The samples were centrifuged at 800×g for 20 min. The mononuclear cells at the boundary layer were transferred into a new centrifuge tube, diluted with 3 times the volume of PBS and centrifuged at 300×g for 5 min. The CD34-positive cells from this cell fraction were isolated using a commercial purification method (CD34 Multisort Kit supplied by Miyltenyi). The CD34-positive cells (6 000–10 000 cells/ml) were resuspended in stem cell medium (0.9% methyl cellulose, 30% calf serum, 1% albumin (bovine), 100 $\mu$M 2-mercapto-ethanol and 2 mM L-glutamine) supplied by StemCell Technologies Inc. 10 mU of human erythropoietin/ml, 10 ng of human IL-3 (interleukin-3)/ml and 0–10 $\mu$M test substance were added. 500 $\mu$l were cultured per well (microtiter plates in each case containing 24 wells) at 37° C. for 14 days and in 5% $CO_2$/95% air.

The cultures were diluted with 20 ml of 0.9% w/v NaCl solution, centrifuged at 600×g for 15 min and resuspended in 200 $\mu$l of 0.9% w/v NaCl. In order to determine the number of erythrocytic cells, 50 $\mu$l of the cell suspension were pipetted into 10 $\mu$l of benzidine staining solution (20 $\mu$g of benzidine in 500 $\mu$l of DMSO, 30 $\mu$l of $H_2O_2$ and 60 $\mu$l of concentrated acetic acid). The number of blue cells was counted with the aid of a microscope.

When the test substances according to the present invention are added, a significant increase in the proliferation of erythrocytic precursor cells is observed in each case.

b) Test description, mouse hematocrit

Normal mice are treated with test substances over several days. The test substances are administered intraperitoneally, subcutaneously or orally. Preferred solvents are Solutol/DMSO/sucrose/NaCl solution or Glycofurol.

From day 0 (prior to the first administration), up to approx. 3 days after the last administration, approx. 70 $\mu$l of blood are withdrawn on several occasions by puncturing the retroorbital venus plexus with a hematocrit capillary. The samples are centrifuged and the hematocrit is determined by reading off manually. The primary parameter is the increase in hematocrit, in relation to the starting value, in the treated animals as compared with the change in the hematocrit in the placebo control (doubly standardized value).

The test substances according to the present invention which are administered lead to a significant increase in the hematocrit.

The novel active compounds can be converted, in a known manner, into the customary formulations, such as tablets, coated tablets, pills, granules, aerosols, syrups, emulsions, suspensions and solutions, using inert, nontoxic, pharmaceutically suitable carrier substances or solvents. In this connection, the therapeutically active compound should in each case be present at a concentration of from about 0.5 to 90% by weight of the total mixture, i.e. in quantities which are sufficient for achieving the given dosing latitude.

The formulations are prepared, for example, by extending the active compounds with solvents and/or carrier substances, where appropriate using emulsifying agents and/or dispersing agents, it being possible, for example when using water as a diluent, to use organic solvents as auxiliary solvents, where appropriate. Administration is effected in a customary manner, preferably orally, transdermally or parenterally, in particular perlingually or intravenously.

In general, it has proved to be advantageous, when administering intravenously, to administer quantities of from about 0.01 to 10 mg/kg, preferably of from about 0.1 to 10 mg/kg, of bodyweight in order to achieve effective results.

Despite this, it can be necessary, where appropriate, to diverge from the quantities mentioned, specifically in dependence on bodyweight or on the nature of the administration route, on the individual reaction to the drug, on the type of formulation and on the time or interval at which the administration takes place. Thus, it can be sufficient, in some cases, to make do with less than the previously mentioned lowest quantity while, in other cases, it is necessary to exceed the abovementioned upper limit. When relatively large quantities are being administered, it can be advisable to divide these quantities into several single doses which are then given during the course of the day.

B PREPARATION EXAMPLES

EXAMPLE I

Preparing the Starting Compound 4-(1,4,5, 6-Tetrahydro-6-oxo-3-pyridazinyl)benzoyl chloride

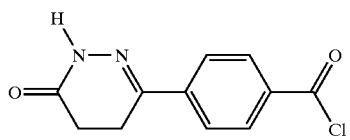

10 mmol (2.2 g) of 4-(1,4,5,6-tetrahydro-6-oxo-3-pyridazinyl)benzoic acid are suspended in 50 ml of dichloromethane, after which 1.5 ml (20 mmol) of thionyl chloride are added and the mixture is stirred for 24 hours while being boiled gently.

The mixture is then cooled down, separated off from insoluble material by being filtered with suction, and inspissated thoroughly. The inspissation residue is stirred up with toluene and filtered off with suction.

This results in 2.0 g of a crude product which is subjected to further reaction without being purified.

EXAMPLE II

Preparing the Starting Compound 4-(4-Methyl-1,4,5,6-tetrahydro-6-oxo-3-pyridazinyl)benzoic imidazolide

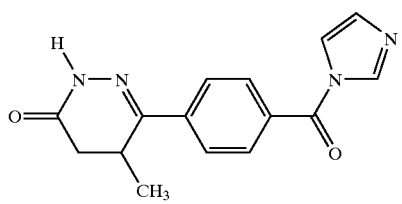

4.7 g (20.24 mmol) of 4-(4-methyl-1,4,5,6-tetrahydro-6-oxo-3-pyridazinyl)benzoic acid are suspended in 120 ml of THF (anhydrous), after which 3.97 g (24.50 mmol) of carbonyldiimidazole are added. This results in a solution from which an oily mass separates out. The mixture is filtered and the filtrate is stirred for a further 3 hours. It is then inspissated, after which the residue is stirred up with a little THF; the solid is then filtered off with suction and washed with THF. This results in 3.9 g of virtually colorless crystals having a melting point of 171–174° C.

EXAMPLE 1
4-(4-Methyl-1,4,5,6-tetrahydro-6-oxo-3-pyridazinyl) benzoic 2-(2-thienylethyl)amide

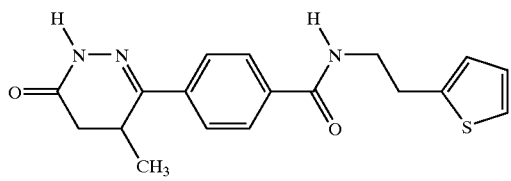

282 mg (1 mmol) of 4-(4-methyl-1,4,5,6-tetrahydro-6-oxo-3-pyridazinyl)benzoic imidazolide from example II are stirred, at 100° C. for 5 hours, in 3 ml of dioxane together with 254 mg (2 mmol) of 2-thienylethylamine. Cooling takes place followed by dissolution in dichloromethane; this solution is then washed twice with 1N hydrochloric acid, with water, with sodium hydrogen carbonate solution and once again with water, and then dried and inspissated. The inspissation residue is crystallized using ethyl acetate. This results in 218 mg (63.8% of theory) of colorless crystals having a melting point of 163–164° C.

EXAMPLE 2

Cyclopentyl 4-(4-methyl-1,4,5,6-tetrahydro-6-oxo-3-pyridazinyl)benzoate

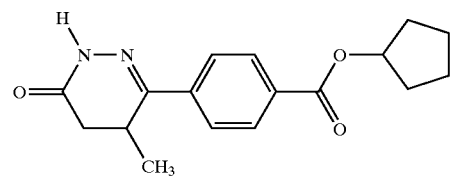

200 mg (0.71 mmol) of 4-(4-methyl-1,4,5,6-tetrahydro-6-oxo-3-pyridazinyl)benzoic imidazolide from example II are stirred, at 100° C. for 24 hours, in 2 ml of dioxane together with 2 ml of cyclopentanol. The mixture is inspissated as far as possible and separated on a column. The clean fractions crystallize using ether/heptane. This results in 53 mg of colorless crystals having a melting point of 120–122° C.

EXAMPLE 3

6-[4-(2-Fluorophenylaminocarbonyl)phenyl]-4,5-dihydro-3(2H)-pyridazinone

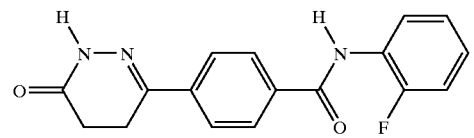

120 mg (0.5 mmol) of 4-(1,4,5,6-tetrahydro-6-oxo-3-pyridazinyl)benzoyl chloride from example I are stirred, at 60° C. for 2 hours, in 5 ml of THF together with 56 mg (0.5 mmol) of 2-fluoroaniline and 0.1 ml of pyridine. The mixture is cooled down and inspissated. The inspissation residue is purified on a silica gel column. The clean fractions are combined, inspissated, crystallized using methanol, filtered-off with suction and washed with methanol. This results in 60 mg of colorless crystals having a melting point of 242–244° C.

The substances listed in the following table are prepared in analogy with the above-mentioned directions given in examples 1 to 3. In the case of the structures in the following table which contain the

radical(s), it is always a

function which is meant.

| Ex. No. | Structure | MW | m.p.: |
|---|---|---|---|
| 4 | 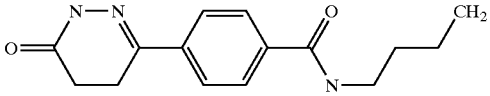 | 273.34 | 217–218 |
| 5 | 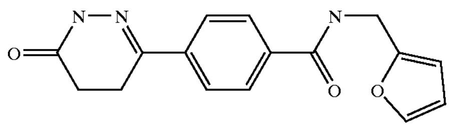 | 297.32 | 208–210 |
| 6 | 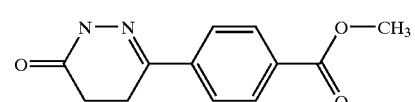 | 232.24 | 203–205 |
| 7 | 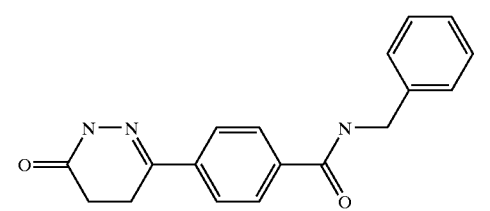 | 307.36 | 208–209 |
| 8 | 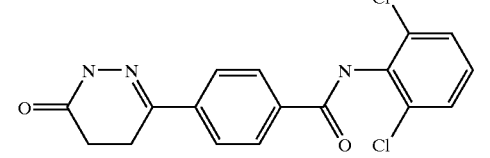 | 362.22 | >250 |
| 9 | 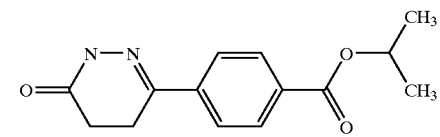 | 260.30 | 155–156 |
| 10 | 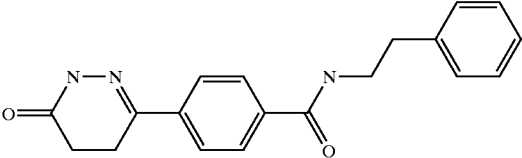 | 321.38 | 223–226 |
| 11 | 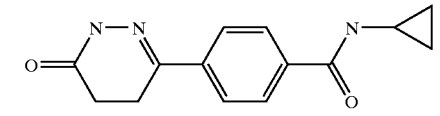 | 257.29 | 248–50 |
| 12 | 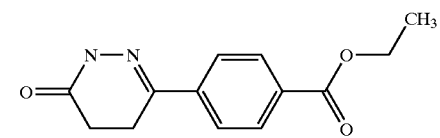 | 246.27 | 157–159 |
| 13 | 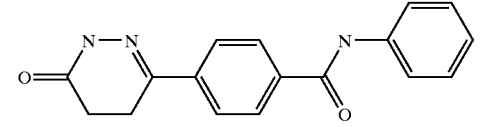 | 293.33 | >250 |

-continued

| Ex. No. | Structure | MW | m.p.: |
|---|---|---|---|
| 14 | (4,5-dihydro-6-oxo-pyridazin-3-yl)phenyl-N-methylbenzamide | 231.26 | 233–234 |
| 15 | (4,5-dihydro-6-oxo-pyridazin-3-yl)phenyl-N-ethylbenzamide | 245.28 | 228–230 |
| 16 | (4,5-dihydro-6-oxo-pyridazin-3-yl)phenyl-N-(naphthalen-1-ylmethyl)benzamide | 357.42 | 258–260 |
| 17 | (4,5-dihydro-6-oxo-pyridazin-3-yl)phenyl-N-(pyridin-2-ylmethyl)benzamide | 308.34 | 228–230 |
| 18 | (4,5-dihydro-6-oxo-pyridazin-3-yl)phenyl-N-(2-chlorophenyl)benzamide | 327.77 | 209–210 |
| 19 | (4,5-dihydro-6-oxo-pyridazin-3-yl)phenyl-piperidin-1-yl-methanone | 285.35 | 182–184 |
| 20 | (4,5-dihydro-6-oxo-pyridazin-3-yl)phenyl-N-(pyridin-3-ylmethyl)benzamide | 308.34 | 220–223 |
| 21 | (4,5-dihydro-6-oxo-pyridazin-3-yl)phenyl-N-(4-methylphenyl)benzamide | 307.36 | >250 |
| 22 | (4,5-dihydro-6-oxo-pyridazin-3-yl)phenyl-N-(3-chlorophenyl)benzamide | 327.77 | >250 |

-continued
| Ex. No. | Structure | MW | m.p.: |
|---|---|---|---|
| 23 | 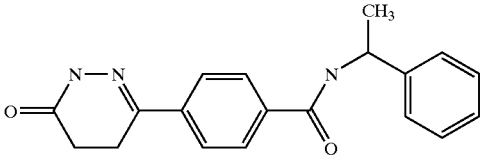 | 321.38 | 242–243 |
| 24 | 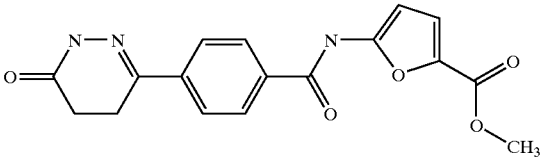 | 341.33 | >260 |
| 25 | 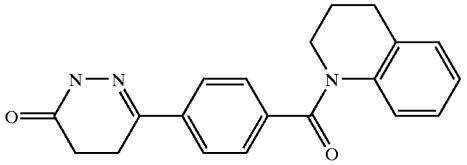 | 333.39 | 215–216 |
| 27 | 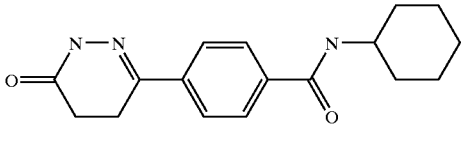 | 299.38 | 249–250 |
| 28 | 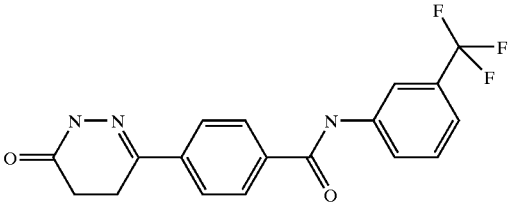 | 361.33 | 229–230 |
| 29 | 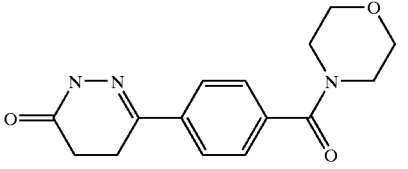 | 287.32 | 202–203 |
| 30 | 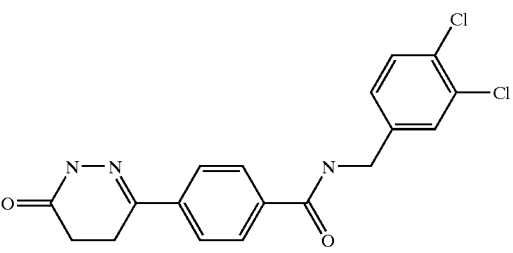 | 376.25 | 208–209 |
| 31 | 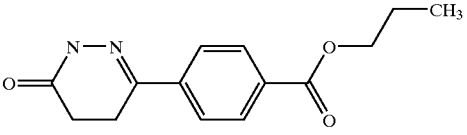 | 260.30 | 283–284 |

-continued

| Ex. No. | Structure | MW | m.p.: |
|---|---|---|---|
| 32 | isobutyl 4-(6-oxo-1,4,5,6-tetrahydropyridazin-3-yl)benzoate | 274.32 | 259–260 |
| 33 | sec-butyl 4-(6-oxo-1,4,5,6-tetrahydropyridazin-3-yl)benzoate | 274.32 | 120–122 |
| 34 | cyclopropylmethyl 4-(6-oxo-1,4,5,6-tetrahydropyridazin-3-yl)benzoate | 272.31 | 158–159 |
| 35 | cyclopentyl 4-(6-oxo-1,4,5,6-tetrahydropyridazin-3-yl)benzoate | 286.33 | 167–169 |
| 36 | allyl 4-(6-oxo-1,4,5,6-tetrahydropyridazin-3-yl)benzoate | 258.28 | 131–133 |
| 37 | 2-(N-benzyl-N-methylamino)ethyl 4-(6-oxo-1,4,5,6-tetrahydropyridazin-3-yl)benzoate | 365.44 | 90–91 |
| 38 | 1-cyclopropylethyl 4-(6-oxo-1,4,5,6-tetrahydropyridazin-3-yl)benzoate | 286.33 | 104–105 |
| 39 | 2-phenylethyl 4-(6-oxo-1,4,5,6-tetrahydropyridazin-3-yl)benzoate | 322.37 | 146–148 |
| 40 | cyclobutylmethyl 4-(6-oxo-1,4,5,6-tetrahydropyridazin-3-yl)benzoate | 286.33 | 155–156 |

-continued
| Ex. No. | Structure | MW | m.p.: |
|---|---|---|---|
| 41 | 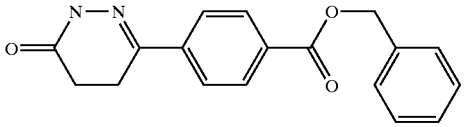 | 308.34 | 156–157 |
| 42 | 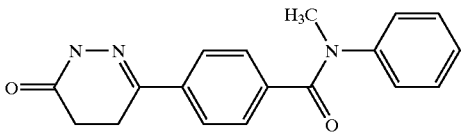 | 307.36 | 208–209 |
| 43 | 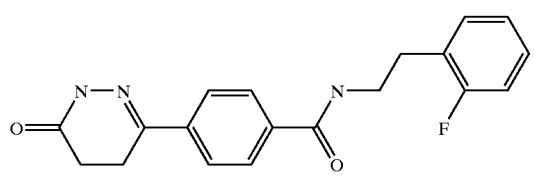 | 339.37 | 189–190 |
| 44 | 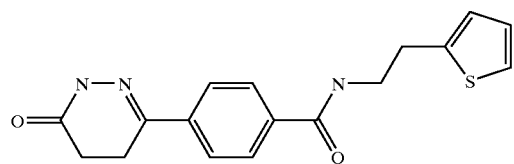 | 327.41 | 215–216 |
| 45 | 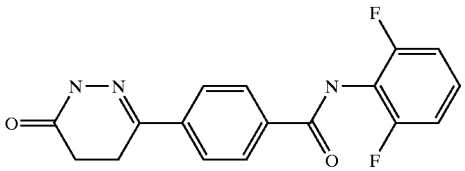 | 329.31 | 278–279 |
| 46 | 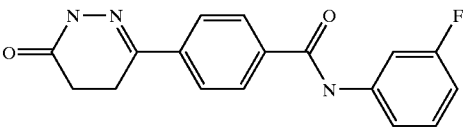 | 311.32 | 260 Z |
| 47 | 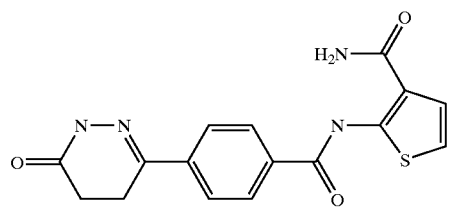 | 342.38 | >250 |
| 48 | 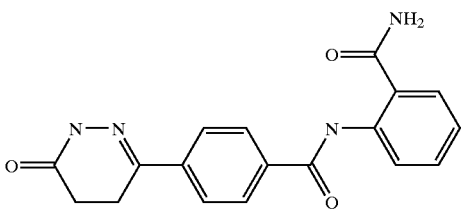 | 336.35 | 283 Z |

-continued

| Ex. No. | Structure | MW | m.p.: |
|---|---|---|---|
| 49 | 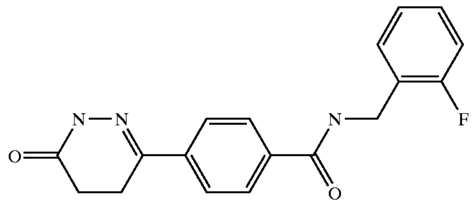 | 325.35 | 186–7 |
| 51 | 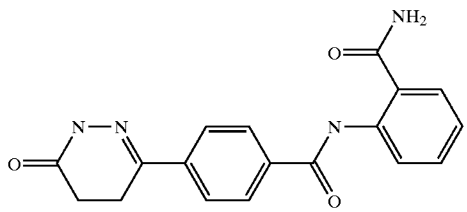 | 336.35 | >250 |
| 52 | 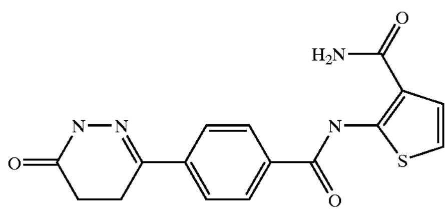 | 342.38 | >250 |
| 53 | 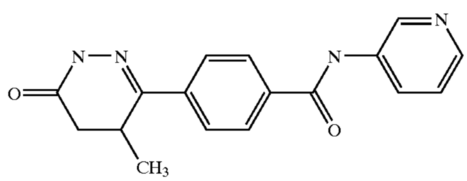 | 308.00 | 267–268 |
| 54 | 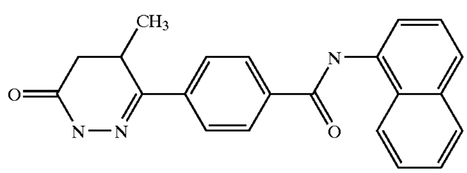 | 357.00 | 266–267 |
| 55 | 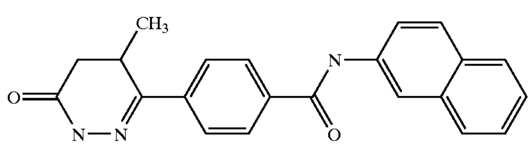 | 357.00 | 271–272 |
| 56 | 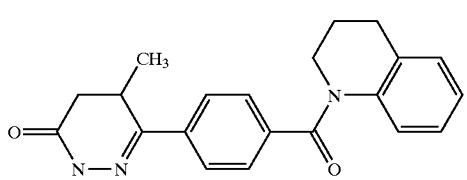 | 347.00 | >260 |
| 57 | 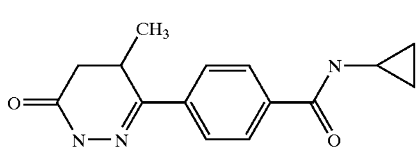 | 271.00 | 216–217 |

-continued

| Ex. No. | Structure | MW | m.p.: |
|---|---|---|---|
| 58 | ![structure] | 301.00 | 152–153 |
| 59 | ![structure] | 411.00 | 186–187 |
| 60 | ![structure] | 365.00 | 245–246 |
| 61 | ![structure] | 365.00 | 164–165 |
| 62 | ![structure] | 287.00 | 166–167 |
| 63 | ![structure] | 395.00 | 146–147 |

What is claimed is:

1. A 6-carboxyphenyldihydropyridazinone derivative of the general formula (I)

(I)

in which

A, D, E and G are identical or different and represent hydrogen, halogen, trifluoromethyl or hydroxyl, or represent ($C_1$–$C_6$)-alkyl or represent ($C_1$–$C_6$)-alkoxy, $R^1$ and $R^2$ are identical or different and represent hydrogen or represent ($C_1$–$C_6$)-alkyl, $R^3$ represents radicals of the formulae —$OR^4$ or —$NR^5R^6$, in which $R^4$ denotes cycloalkyl having from 3 to 8 carbon atoms or ($C_1$–$C_8$)-alkyl which is optionally substituted by hydroxyl, ($C_1$–$C_6$)-alkoxy, cycloalkyl having from 3 to 8 carbon atoms or aryl having from 6 to 10 carbon atoms which, for its part, can be substituted, once to twice, identically or differently, by substituents which are selected from the group consisting of halogen, ($C_1$–$C_6$)-alkoxy, hydroxyl and trifluoromethyl, or denotes ($C_1$–$C_8$)-alkyl which is optionally substituted by a group of the formula —$NR^7R^8$, in which $R^7$ and $R^8$ are identical or different and denote hydrogen, ($C_1$–$C_6$)-alkyl or benzyl, or $R^4$ denotes vinyl or allyl, or $R^4$ denotes aryl having from 6 to 10 carbon atoms which is optionally substituted, once to twice, identically or differently, by substituents which are selected from the group consisting of halogen, ($C_1$–$C_6$)-alkyl, ($C_1$–$C_6$)-alkoxy and hydroxyl, $R^5$ denotes hydrogen or ($C_1$–$C_4$)-alkyl, $R^6$ denotes cycloalkyl having from 3 to 8 carbon atoms or a radical of the formula or aryl having from 6 to 10 carbon atoms or a pyridyl, thienyl, pyridazinyl, furyl, or thiazolyl group, it being possible for the ring systems which are listed here to be optionally substituted, once to several times, identically or differently, by substituents which are selected from the group consisting of halogen, trifluoromethyl, hydroxyl, ($C_1$–$C_6$)-alkoxy, carboxyl, ($C_1$–$C_6$)-alkoxycarbonyl, ($C_1$–$C_6$)-alkyl and radicals of the formulae —$SO_2$—$NR^9R^{10}$ and —$(CO)_a$—$NR^{11}R^{12}$, in which $R^9$, $R^{10}$, $R^{11}$ and $R^{12}$ are identical or different and denote hydrogen or ($C_1$–$C_6$)-alkyl, and a denotes a number 0 or 1, or $R^6$ denotes ($C_1$–$C_8$)-alkyl which is substituted, once to twice, identically or differently, by substituents which are selected from the group consisting of halogen, trifluoromethyl, hydroxyl, ($C_1$–$C_6$)-alkoxy, carboxyl, ($C_1$–$C_6$)-alkoxycarbonyl, aryl having from 6 to 10 carbon atoms, pyridyl, thienyl, pyridazinyl, furyl, and thiazolyl, in which the ring systems can be optionally substituted, once to three times, identically or differently, by ($C_1$–$C_6$)-alkyl, halogen, ($C_1$–$C_6$)-alkoxy, ($C_1$–$C_6$)-alkoxycarbonyl, trifluoromethyl or by the radical —CO—$NH_2$, or $R^5$ and $R^6$ form, together with the nitrogen atom, cyclic radicals of the formulae or a pharmaceutically acceptable salt thereof.

2. The 6-carboxyphenyldihydropyridazinone derivative of claim 1, wherein in the general formula (I)

A, D, E and G are-identical or different and represent hydrogen, fluorine, chlorine, bromine or trifluoromethyl, $R^1$ and $R^2$ are identical or different and represent hydrogen or represent methyl, $R^3$ represents radicals of the formulae —$OR^4$ or —$NR^5R^6$, in which $R^4$ denotes cyclopropyl, cyclopentyl or cyclohexyl or denotes ($C_1$–$C_6$)-alkyl which is optionally substituted by hydroxyl, ($C_1$–$C_4$)-alkoxy, cyclopropyl, cyclopentyl, cyclohexyl or phenyl which, for its part, can be substituted once to twice, identically or differently, by substituents selected from the group consisting of fluorine, chlorine, bromine, ($C_1$–$C_4$)-alkoxy, hydroxyl and trifluoromethyl, or denotes ($C_1$–$C_6$)-alkyl which is optionally substituted by a group of the formula —$NR^7R^8$, in which $R^7$ and $R^8$ are identical or different and denote hydrogen or ($C_1$–$C_4$)-alkyl, or $R^4$ denotes allyl, $R^5$ denotes hydrogen or ($C_1$–$C_3$)-alkyl, $R^6$ denotes cyclopropyl, cyclopentyl or cyclohexyl or denotes phenyl, thienyl, thiazolyl, furyl or pyridyl, it being possible for the listed aromatic ring systems to be optionally substituted, once to twice, identically or differently, by substituents selected from the group consisting of fluorine, chlorine, bromine, trifluoromethyl, hydroxyl, ($C_1$–$C_3$)-alkoxy, ($C_1$–$C_3$)-alkoxycarbonyl, ($C_1$–$C_4$)-alkyl and radicals of the formulae —$SO_2NR^9R^{10}$ and —$(CO)_a$—$NR^{11}R^{12}$, in which $R^9$, $R^{10}$, $R^{11}$ and $R^{12}$ are identical or different and denote hydrogen or ($C_1$–$C_4$)-alkyl, and a denotes a number 0 or 1, or $R^6$ denotes ($C_1$–$C_6$)-alkyl which is substituted once to twice, identically or differently, by substituents selected from the group consisting of fluorine, chlorine, bromine, trifluoromethyl, hydroxyl, ($C_1$–$C_4$)-alkoxy, ($C_1$–$C_4$)-alkoxycarbonyl, phenyl, pyridyl, naphthyl, furyl and thiazolyl, it being possible for the ring systems to be optionally substituted, once to twice, identically or differently, by fluorine, chlorine, methyl, methoxycarbonyl, trifluoromethyl or by a radical of the formula —CO—NH$_2$) or $R^5$ and $R^6$ form, together with the nitrogen atom, cyclic radicals of the formulae

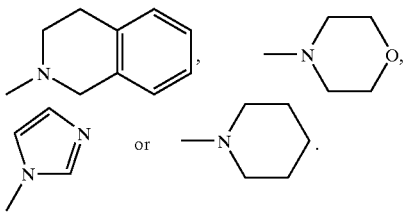

3. The 6-carboxyphenyldihydropyridazinone derivative of claim 1, wherein in the general formula (I)

A, D, E and G represent hydrogen, $R^1$ and $R^2$ are identical or different and represent hydrogen or represent methyl, $R^3$ represents radicals of the formulae —OR$^4$ or —NR$^5$R$^6$, in which $R^4$ denotes cyclopropyl, cyclopentyl or cyclohexyl or denotes (C$_1$–C$_5$)-alkyl which is optionally substituted by (C$_1$–C$_4$)-alkoxy, cyclopropyl, cyclopentyl, cyclohexyl or phenyl which, for its part, can be substituted, once to twice, identically or differently, by substituents selected from the group consisting of fluorine, chlorine, (C$_1$–C$_4$)-alkoxy, hydroxyl and trifluoromethyl, or denotes (C$_1$–C$_4$)-alkyl which is optionally substituted by a group of the formula —NR$^7$R$^8$, in which $R^7$ and $R^8$ are identical or different and denote hydrogen, benzyl or methyl, or $R^4$ denotes allyl, $R^5$ denotes hydrogen or (C$_1$–C$_3$)-alkyl, $R^6$ denotes cyclopropyl, cyclopentyl or cyclohexyl or denotes naphthyl, phenyl, thienyl, thiazolyl, furyl or pyridyl, the listed ring systems being optionally substituted once to twice, identically or differently, by substituents selected from the group consisting of fluorine, chlorine, bromine, trifluoromethyl, (C$_1$–C$_3$)-alkoxy, (C$_1$–C$_3$)-alkoxycarbonyl, (C$_1$–C$_3$)-alkyl and radicals of the formulae —SO$_2$—NR$^9$R$^{10}$ and —(CO)$_a$—NR$^{11}$R$^{12}$, in which $R^9$, $R^{10}$, $R^{11}$ and $R^{12}$ are identical or different and denote hydrogen or (C$_1$–C$_4$)-alkyl, and a denotes a number 0 or 1, or $R^6$ denotes (C$_1$–C$_6$)-alkyl which is substituted by substituents selected from the group consisting of fluorine, chlorine, trifluoromethyl, (C$_1$–C$_3$)-alkoxy, (C$_1$–C$_3$)-alkoxycarbonyl, phenyl, pyridyl, naphthyl, furyl, thienyl and thiazolyl, the ring systems optionally being substituted once to twice, identically or differently, by fluorine, chlorine, methyl, methoxycarbonyl or trifluoromethyl or by a radical of the formula —CO—NH$_2$, or $R^5$ and $R^6$ form, together with the nitrogen atom, cyclic radicals of the formulae

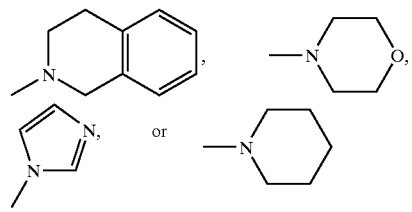

4. The 6-carboxyphenyldihydropyridazinone derivative of claim 1, wherein in the general formula (I)

A, D, E and G represent hydrogen, $R^3$ represents the radical —NR$^5$R$^6$, where $R^5$=H or methyl and $R^6$ is as defined in claim 1, and the remaining radicals have the meanings defined in claim 1.

5. A process for preparing 6-carboxy-phenyl-dihydropyridazinone derivatives of formula (I) as defined in claim 1

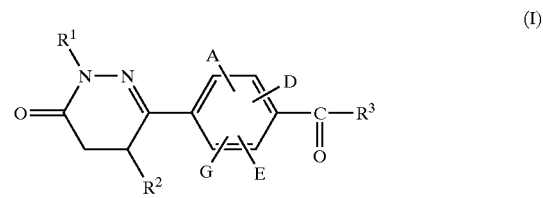

characterized in that (A) in the case where $R^3$ represents the radical of the formula —OR$^4$ in general formula (I), a compound of the general formula (II)

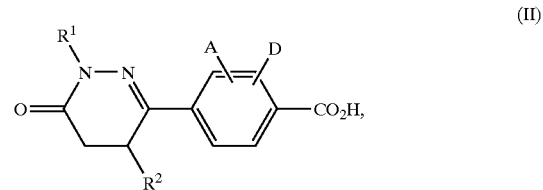

in which

A, D, $R^1$ and $R^2$ are as defined in claim 1, is initially converted, by reaction with a carboxylic acid-activating reagent using customary methods, into a compound of the general formula (IV)

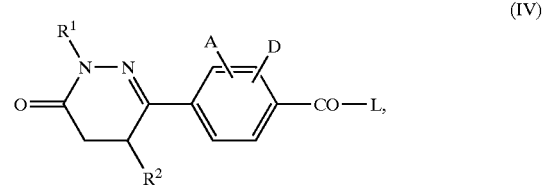

in which

A, D, $R^1$ and $R^2$ are as defined in claim 1, and

L represents an activating radical, and, in a second step, reacted with a compound of the general formula (III), $$HO-R^4 \quad (III),$$

in which
R$^4$ is as defined in claim 1,
in an inert solvent, where appropriate in the presence of a base, or
(B) in the case where R$^3$ represents the radical of the formula —NR$^5$R$^6$ in the above general formula (I), a compound of the general formula (II) is initially converted, by reaction with a carboxylic acid-activating reagent, and using customary methods, into a compound of the general formula (IV)

(IV)

[Chemical structure: dihydropyridazinone with R$^1$, R$^2$, A, D substituents and CO—L group]

in which
A, D, R$^1$ and R$^2$ are as defined in claim 1, and
L represents an activating radical,
and, in a second step, reacted with an amine of the general formula (V)

$$HNR^5R^6 \quad (V),$$

in which
R$^5$ and R$^6$ are as defined in claim 1,
in an inert solvent.

6. A pharmaceutical composition which comprises at least one compound of claim 1, and also one or more pharmacologically acceptable excipients.

7. A method for prophylaxis or treatment of anemia comprising administering to a subject an effective amount of a 6-carboxyphenyldihydropyridazinone derivative of the general formula (I)

(I)

[Chemical structure with R$^1$, R$^2$, A, D, E, G substituents and C(=O)—R$^3$ group]

in which
A, D, E and G are identical or different and represent hydrogen, halogen, trifluoromethyl or hydroxyl, or represent (C$_1$–C$_6$)-alkyl or represent (C$_1$–C$_6$)-alkoxy,
R$^1$ and R are identical or different and represent hydrogen or represent (C$_1$–C$_6$)-alkyl,
R$^3$ represents radicals of the formulae —OR$^4$ or —NR$^5$R$^6$,
in which
R$^4$ denotes cycloalkyl having from 3 to 8 carbon atoms or (C$_1$–C$_8$)-alkyl which is optionally substituted by hydroxyl, (C$_1$–C$_6$)-alkoxy, cycloalkyl having from 3 to 8 carbon atoms or aryl having from 6 to 10 carbon atoms which, for its part, can be substituted, once to twice, identically or differently, by substituents which are selected from the group consisting of halogen, (C$_1$–C$_6$)-alkoxy, hydroxyl and trifluoromethyl, or denotes (C$_1$–C$_8$)-alkyl which is optionally substituted by a group of the formula —NR$^7$R$^8$,
in which
R$^7$ and R$^8$ are identical or different and denote hydrogen, (C$_1$–C$_6$)-alkyl or benzyl, or
R$^4$ denotes vinyl or allyl, or
R$^4$ denotes aryl having from 6 to 10 carbon atoms which is optionally substituted, once to twice, identically or differently, by substituents which are selected from the group consisting of halogen, (C$_1$–C$_6$)-alkyl, (C$_1$–C$_6$)-alkoxy and hydroxyl,
R$^5$ denotes hydrogen or (C$_1$–C$_4$)-alkyl,
R$^6$ denotes cycloalkyl having from 3 to 8 carbon atoms or a radical of the formula

[Chemical structure: tetrahydrobenzothiophene] or aryl having from 6 to 10 carbon atoms or a pyridyl, thienyl, pyridazinyl, furyl, or thiazolyl group, it being possible for the ring systems which are listed here to be optionally substituted, once to several times, identically or differently, by substituents which are selected from the group consisting of halogen, trifluoromethyl, hydroxyl, (C$_1$–C$_6$)-alkoxy, carboxyl, (C$_1$–C$_6$)-alkoxycarbonyl, (C$_1$–C$_6$)-alkyl and radicals of the formulae —SO$_2$—NR$^9$R$^{10}$ and —(CO)$_a$—NR$^{11}$R$^{12}$,
in which
R$^9$, R$^{10}$, R$^{11}$ and R$^{12}$ are identical or different and denote hydrogen or (C$_1$–C$_6$)-alkyl, and
a denotes a number 0 or 1, or
R$^6$ denotes (C$_1$–C$_8$)-alkyl which is optionally substituted, once to twice, identically or differently, by substituents which are selected from the group consisting of halogen, trifluoromethyl, hydroxyl, (C$_1$–C$_6$)-alkoxy, carboxyl, (C$_1$–C$_6$)-alkoxycarbonyl, aryl having from 6 to 10 carbon atoms, pyridyl, thienyl, pyridazinyl, furyl, and thiazolyl, in which the ring systems can be optionally substituted, once to three times, identically or differently, by (C$_1$–C$_6$)-alkyl, halogen, (C$_1$–C$_6$)-alkoxy, (C$_1$–C$_6$)-alkoxycarbonyl, trifluoromethyl or by the radical —CO—NH$_2$, or
R$^5$ and R$^6$ form, together with the nitrogen atom, cyclic radicals of the formulae

[Chemical structures: tetrahydroisoquinoline, morpholine, imidazole, piperidine]

or a pharmaceutically acceptable salt thereof.

8. The method of claim 7 wherein in the 6-carboxyphenyldihydropyridazinone derivative of the general formula (I)
A, D, E and G are identical or different and represent hydrogen, fluorine, chlorine, bromine or trifluoromethyl,
R$^1$ and R$^2$ are identical or different and represent hydrogen or represent methyl, R³ represents radicals of the formulae —OR⁴ or —NR⁵R⁶, in which R⁴ denotes cyclopropyl, cyclopentyl or cyclohexyl or denotes $(C_1-C_6)$-alkyl which is optionally substituted by hydroxyl, $(C_1-C_4)$-alkoxy, cyclopropyl, cyclopentyl, cyclohexyl or phenyl which, for its part, can be substituted once to twice, identically or differently, by substituents selected from the group consisting of fluorine, chlorine, bromine, $(C_1-C_4)$-alkoxy, hydroxyl and trifluoromethyl, or denotes $(C_1-C_6)$-alkyl which is optionally substituted by a group of the formula —NR⁷R⁸, in which R⁷ and R⁸ are identical or different and denote hydrogen or $(C_1-C_4)$-alkyl, or R⁴ denotes vinyl or allyl, R⁵ denotes hydrogen or $(C_1-C_3)$-alkyl, R⁶ denotes cyclopropyl, cyclopentyl or cyclohexyl or denotes phenyl, thienyl, thiazolyl, furyl or pyridyl, it being possible for the listed aromatic ring systems to be optionally substituted, once to twice, identically or differently, by substituents selected from the group consisting of fluorine, chlorine, bromine, trifluoromethyl, hydroxyl, $(C_1-C_3)$-alkoxy, $(C_1-C_3)$-alkoxycarbonyl, $(C_1-C_4)$-alkyl and radicals of the formulae —SO₂NR⁹R¹⁰ and —(CO)$_a$—NR¹¹R¹², in which R⁹, R¹⁰, R¹¹ and R¹² are identical or different and denote hydrogen or $(C_1-C_4)$-alkyl, and a denotes a number 0 or 1, or R⁶ denotes $(C_1-C_6)$-alkyl which are optionally substituted once to twice, identically or differently, by substituents selected from the group consisting of fluorine, chlorine, bromine, trifluoromethyl, hydroxyl, $(C_1-C_4)$-alkoxy, $(C_1-C_4)$-alkoxycarbonyl, phenyl, pyridyl, naphthyl, furyl and thiazolyl, it being possible for the ring systems to be optionally substituted, once to twice, identically or differently, by fluorine, chlorine, methyl, methoxycarbonyl, trifluoromethyl or by a radical of the formula —CO—NH₂, or R⁵ and R⁶ form, together with the nitrogen atom, cyclic radicals of the formulae 9. The method of claim 7 wherein in the 6-carboxyphenyldihydropyridazinone derivatives of the general formula (I)

A, D, E and G represent hydrogen,

R¹ and R² are identical or different and represent hydrogen or represent methyl, R³ represents radicals of the formulae —OR⁴ or —NR⁵R⁶, in which R⁴ denotes cyclopropyl, cyclopentyl or cyclohexyl or denotes $(C_1-C_5)$-alkyl which is optionally substituted by $(C_1-C_4)$-alkoxy, cyclopropyl, cyclopentyl, cyclohexyl or phenyl which, for its part, can be substituted, once to twice, identically or differently, by substituents selected from the group consisting of fluorine, chlorine, $(C_1-C_4)$-alkoxy, hydroxyl and trifluoromethyl, or denotes $(C_1-C_4)$-alkyl which is optionally substituted by a group of the formula —NR⁷R⁸, in which R⁷ and R⁸ are identical or different and denote hydrogen, benzyl or methyl, or R⁴ denotes allyl, R⁵ denotes hydrogen or $(C_1-C_3)$-alkyl, R⁶ denotes cyclopropyl, cyclopentyl or cyclohexyl or denotes naphthyl, phenyl, thienyl, thiazolyl, furyl or pyridyl, the listed ring systems being optionally substituted once to twice, identically or differently, by substituents selected from the group consisting of fluorine, chlorine, bromine, trifluoromethyl, $(C_1-C_3)$-alkoxy, $(C_1-C_3)$-alkoxycarbonyl, $(C_1-C_3)$-alkyl and radicals of the formulae —SO₂—NR⁹R¹⁰ and-(CO)₆-NR¹¹R¹², in which R⁹, R¹⁰, R¹¹ and R¹² are identical or different and denote hydrogen or $(C_1-C_4)$-alkyl, and a denotes a number 0 or 1, or R⁶ denotes $(C_1-C_6)$-alkyl which is optionally substituted by substituents selected from the group consisting of fluorine, chlorine, trifluoromethyl, $(C_1-C_3)$-alkoxy, $(C_1-C_3)$-alkoxycarbonyl, phenyl, pyridyl, naphthyl, furyl, thienyl and thiazolyl, the ring systems optionally being substituted once to twice, identically or differently, by fluorine, chlorine, methyl, methoxycarbonyl or trifluoromethyl or by a radical of the formula —CO—NH₂, or R⁵ and R⁶ form, together with the nitrogen atom, cyclic radicals of the formulae 10. The method of claim 7 wherein in the 6-carboxyphenyldihydropyridazinone derivatives of the general formula (I)

A, D, E and G represent hydrogen,

R³ represents the radical —NR⁵R⁶, where R⁵=H or methyl and R⁶ is as defined in claim 7, and the remaining radicals are as defined in claim 7.

11. The method as claimed in one of claims 7 to 10 wherein the anemia is selected from the group consisting of premature baby anemias, anemias associated with chronic renal insufficiency, anemias following chemotherapy and anemias in HIV patients.

12. The method as claimed in one of claims 7 to 10 wherein the anemia results from individuals donating their own blood and the treatment is to stimulate erythropoesis.

13. The method as claimed in one of claims 7 to 10, characterized in that the 6-carboxyphenyldihydropyridazinone derivative is administered orally.

14. The process of claim 5 wherein in structure (IV), the activating radical L is chlorine or imidazoyl.

* * * * *